US012691000B2

(12) United States Patent
Fallon

(10) Patent No.: US 12,691,000 B2
(45) Date of Patent: Jul. 28, 2026

(54) MULTI-DIRECTIONAL JAW DISPLACEMENT ORAL APPLIANCE

(71) Applicant: John M Fallon, Henderson, NV (US)

(72) Inventor: John M Fallon, Henderson, NV (US)

( * ) Notice: Subject to any disclaimer, the term of this patent is extended or adjusted under 35 U.S.C. 154(b) by 583 days.

(21) Appl. No.: 18/091,980

(22) Filed: Dec. 30, 2022

(65) Prior Publication Data

US 2024/0216164 A1     Jul. 4, 2024

(51) Int. Cl.
*A61F 5/56* (2006.01)
*A61C 7/36* (2006.01)
*A61C 9/00* (2006.01)

(52) U.S. Cl.
CPC ................ *A61F 5/566* (2013.01); *A61C 7/36* (2013.01); *A61C 9/0006* (2013.01)

(58) Field of Classification Search
CPC   A61C 7/08; A61C 7/36; A61C 9/0006; A61F 5/566
USPC ......................................................... 128/848
See application file for complete search history.

(56) References Cited

U.S. PATENT DOCUMENTS 4,601,101 A * 7/1986 McGready .............. B26B 21/52
                                                          30/40
5,570,704 A * 11/1996 Buzzard .................. A61F 5/566
                                                          128/848

8,833,374 B2     9/2014 Fallon et al.
9,427,037 B1 *   8/2016 Atherton ................... A41F 1/00
10,390,990 B2    8/2019 Miguel
10,849,783 B2   12/2020 Fallon et al.
11,311,407 B1    4/2022 Fallon
2010/0242970 A1 * 9/2010 Schmitt-Bylandt ..... A61F 5/566
                                                          128/848
2018/0036165 A1 * 2/2018 Fallon ...................... A61F 5/566
2019/0216632 A1 * 7/2019 Fallon ...................... A61F 5/566

FOREIGN PATENT DOCUMENTS

KR        20190018275 A  *  2/2019   ............... A61F 5/56
KR        101710840        8/2019

* cited by examiner

*Primary Examiner* — Alireza Nia
*Assistant Examiner* — Michael Milo
(74) *Attorney, Agent, or Firm* — Morland C. Fischer

(57) ABSTRACT

Disclosed is a multi-directional jaw displacement oral appliance that includes an upper arch tray assembly coupled to a user's upper set of teeth and a lower arch tray assembly coupled to the user's lower set of teeth. An intermediate arch tray assembly is located between the upper and lower arch tray assemblies. The upper arch tray assembly is connected to the intermediate arch tray assembly by a hinge such that the upper arch tray assembly cannot be separated from the intermediate arch tray assembly and the upper arch tray assembly is rotatable through an angle with the user's upper set of teeth upwardly relative to the intermediate and lower arch tray assemblies. The lower arch tray assembly is adapted to move with the user's lower set of teeth in a horizontal direction by which the position of the user's lower jaw is adjusted to maintain an airway to the user's throat.

14 Claims, 8 Drawing Sheets

MULTI-DIRECTIONAL JAW DISPLACEMENT ORAL APPLIANCE

BACKGROUND OF THE INVENTION

1. Field of the Invention

This invention relates to a multi-directional jaw displacement oral appliance to be worn in the mouth and over the teeth of a user during sleep to reduce the effects of sleep apnea. The jaw displacement oral appliance includes upper and lower arch tray assemblies within which the user's upper and lower sets of teeth are received and an intermediate arch tray assembly located therebetween. The lower arch tray assembly is adapted to move horizontally (i.e., back and forth) with the user's lower set of teeth, and the upper arch tray assembly is pivotally coupled to the intermediate arch tray assembly by a hinge so as to be rotatable through an angle and movable vertically (i.e., up and down) with the user's upper set of teeth relative to the intermediate and lower arch tray assemblies while remaining at all times connected to the intermediate arch tray assembly. By virtue of the foregoing, the upper arch tray assembly will remain in engagement with the user's upper set of teeth should the user open his mouth while asleep. Moreover, the position of the user's lower jaw can be adjusted forward of the upper jaw in order to maintain an open airway to the user's throat.

2. Background Art

Oral appliances are known to be inserted in the mouth and worn over the teeth of a user to maintain an open airway that runs through the appliance to the user's throat to improve the user's breathing during sleep. Examples of such oral appliances are available by referring to U.S. Pat. No. 8,833,374 issued Sep. 16, 2014 and U.S. Pat. No. 10,849,783 issued Dec. 1, 2020. The aforementioned patented oral appliances have particular application for use by those wishing to reduce the effects of snoring and/or sleep apnea. Each appliance includes upper and lower arch tray assemblies against which the user's upper and lower sets of teeth are seated during use. The lower arch tray assembly is slidably adjustable in a horizontal direction relative to the upper arch tray assembly to correspondingly advance the position of the user's lower jaw relative to the user's upper jaw in order to keep the aforementioned airway open to the user's throat as the user's condition changes over time.

Depending upon how the user sleeps and moves about, the position of the oral appliance could shift in the user's mouth relative to his upper and lower sets of teeth. In particular, if the user were to open his mouth while asleep, the upper arch tray assembly of the appliance could separate from the user's upper set of teeth. In that case, when the user closes his mouth, the appliance may be out of alignment with the user's upper set of teeth which could reduce the effectiveness of the appliance by no longer maintaining the user's lower jaw ahead of the upper jaw. In U.S. Pat. No. 10,849,783 referred to above, the upper arch tray assembly is adapted to slide vertically (i.e., up and down) along a post relative to the lower arch tray assembly by which to enable the upper arch tray assembly of the oral appliance to continue to engage the user's upper set of teeth throughout the night whether the user's mouth is open or closed so that an open airway is maintained.

My patent Ser. No. 11/311,407 that issued on Apr. 26, 2022 describes a bidirectional jaw displacement oral appliance having upper and lower arch tray assemblies and an intermediate arch tray assembly located therebetween. The user's upper set of teeth engage the upper arch tray assembly, and the user's lower set of teeth engage the lower arch tray assembly. The upper arch tray assembly is pivotally coupled to the intermediate arch tray by means of coupling hooks that project downwardly from the upper arch tray assembly for removable receipt within openings formed in the intermediate arch tray assembly so that the upper arch tray assembly can rotate with the user's upper set of teeth when the user's mouth is opened during sleep. By virtue of the foregoing, the user's upper set of teeth are not likely to separate from the upper arch tray assembly. In this same regard, the lower arch tray assembly is adapted to slide horizontally by which the position of the user's lower set of teeth and lower jaw can be selectively adjusted relative to the user's upper jaw to maintain an open air path to the user's throat.

Nevertheless, what would be desirable is a modification to my patented oral appliance described above so that the upper and the intermediate arch tray assemblies are pivotally connected to one another, but the upper arch tray assembly is not removable from the intermediate arch tray assembly. In this case, the upper arch tray assembly will not be likely to float free within the user's mouth should the user's mouth be repeatedly opened and closed throughout the night.

SUMMARY OF THE INVENTION

In general terms, a multi-directional jaw displacement oral appliance is disclosed to be worn in the mouth and over the teeth of a user during sleep to reduce the effects of sleep apnea. The oral appliance includes upper and lower arch tray assemblies and a flexible intermediate arch tray assembly located therebetween. Each of the arch tray assemblies has an arcuate configuration with a closed front end and an opposite rear end having a pair of sides spaced from one another to match the bite pattern of the user's teeth. Each of the upper and lower arch tray assemblies includes a tooth impression liner within which the user's upper and lower sets of teeth are received during sleep.

Located at each side of the open rear end of the arcuate upper arch tray assembly is a cylindrical coupling catch having a catch hole running laterally therethrough. Located at each side of the open rear end of the arcuate intermediate arch tray assembly is a pair of flexible coupling pins that are axially aligned and spaced from one another. During the assembly of the oral appliance, the open ends of the upper and intermediate arch tray assemblies are pushed towards one another until the pair of flexible coupling pins are snapped into locking engagement with the coupling catch within the catch hole thereof. By virtue of the snap-in connection of the coupling pins to the locking catch, a hinge is formed by which the upper arch tray assembly is pivotally coupled to the intermediate arch tray assembly so that the closed front end of the upper arch tray assembly is rotatable with the user's upper set of teeth in a vertical direction relative to the intermediate and lower arch tray assemblies. What is more, the upper arch tray assembly is not likely to become inadvertently separated from the intermediate arch tray assembly and float free in the user's mouth during the night.

A pair of position control blocks are located on top and at the opposite sides of the lower arch tray assembly for slidable receipt within respective locking channels that are formed on the bottom and at the opposite sides of the intermediate arch tray assembly. Each of the position adjustment blocks and the locking channels has a set of teeth which run along one side thereof to be moved into mating engagement with one another so as to hold the position adjustment blocks within the locking channels and thereby connect the intermediate arch tray to the lower arch tray assembly.

When it is desirable to move the lower arch tray assembly of the multi-directional jaw displacement oral appliance in a horizontal direction relative to each of the upper arch tray assembly and the intermediate arch tray assembly so that the user's lower jaw can be repositioned relative to the upper jaw, squeezing forces are momentarily applied to the opposite sides of the flexible intermediate arch tray assembly. As a result of the squeezing forces, the flexible intermediate arch tray assembly is momentarily compressed such that the teeth at one side of the locking channels thereof are moved out of their former mating engagement with the teeth at one side of the position adjustment blocks of the lower arch tray assembly. A pushing force is now applied to the lower arch tray assembly to cause the position control blocks thereof to slide through the locking channels of the intermediate arch tray assembly such that the lower arch tray assembly and the user's lower jaw slide forward relative to the upper arch tray assembly and the user's upper jaw. Once the position of the lower arch tray assembly and the user's lower jaw has been adjusted as necessary to meet the needs of the user, the squeezing forces being applied to the intermediate arch tray assembly are terminated. Accordingly, the flexible intermediate arch tray assembly will now automatically expand back to its original shape, whereby the teeth of the locking channels will move back into their mating engagement with the teeth of the position adjustment blocks to once again hold the intermediate and lower arch tray assemblies in place one above the other.

4

Figure 9:
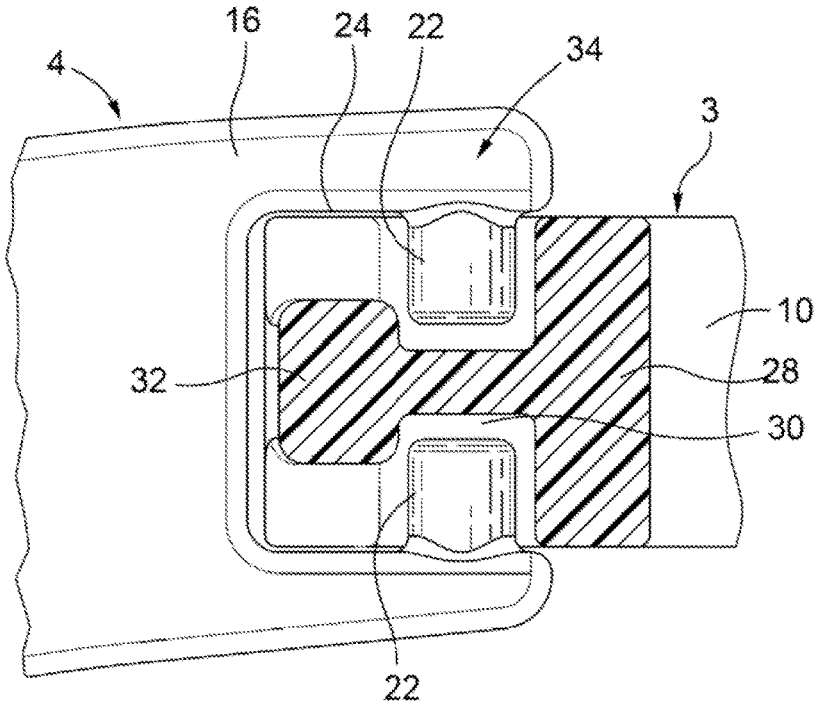
FIG. 9 shows a hinge that is created when the pair of coupling pins of FIG. 8 are snapped into interlocking engagement with the coupling catch of FIG. 8.
Figure 10:
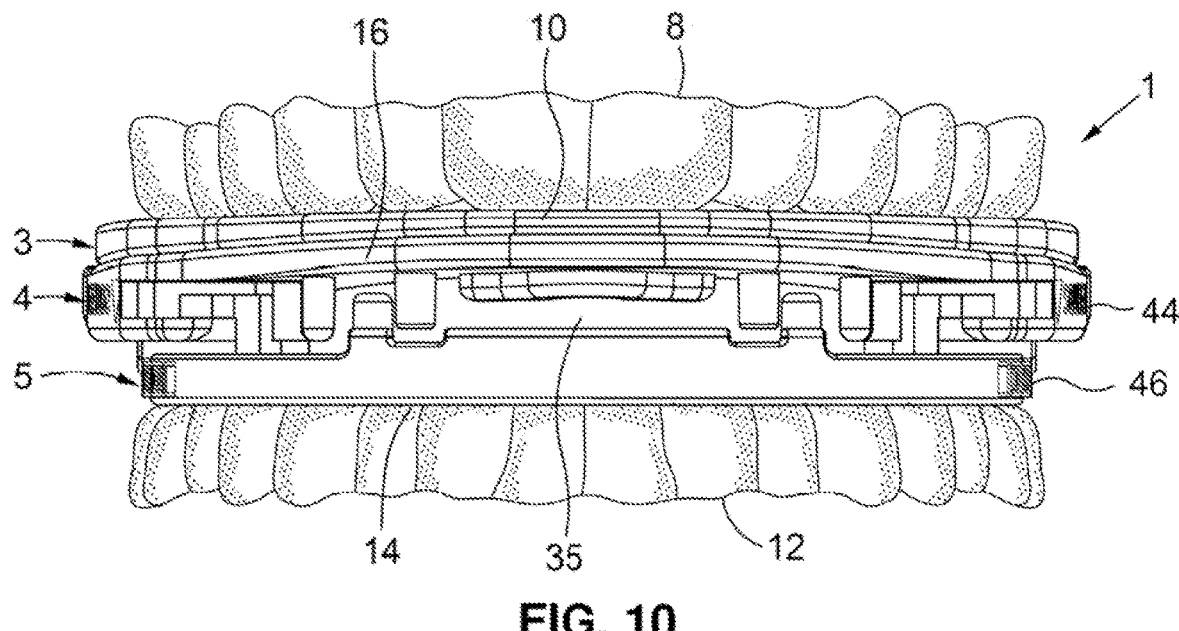
Figure 11:
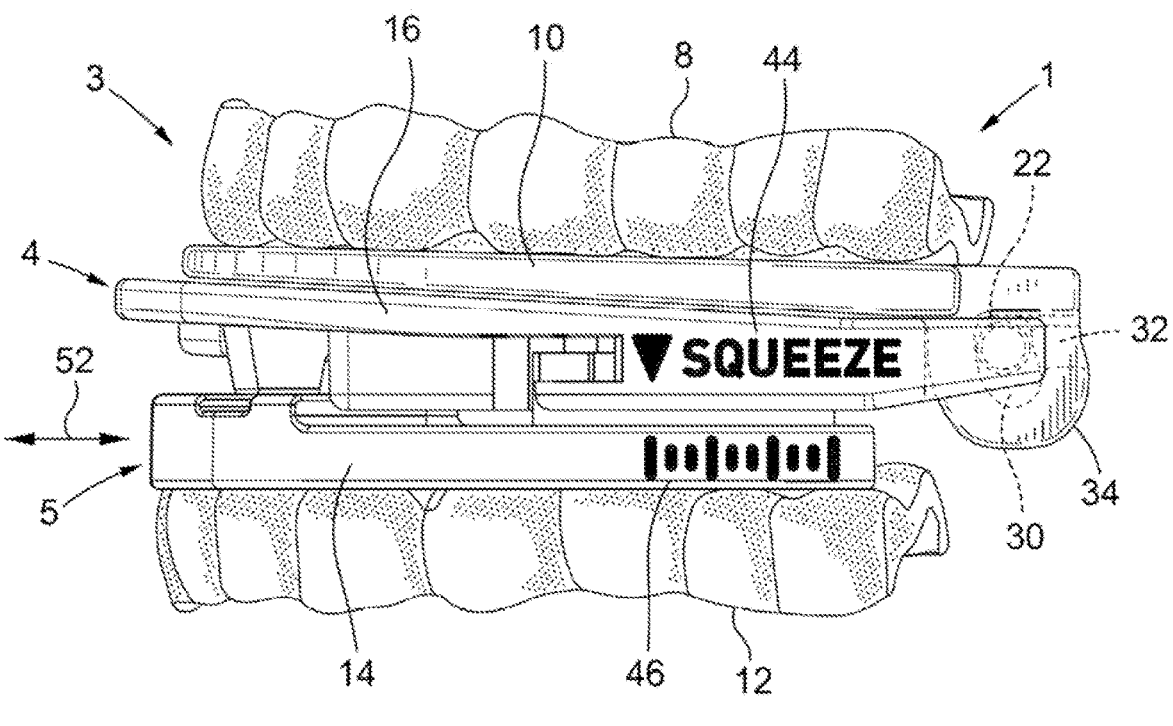
Figure 12:
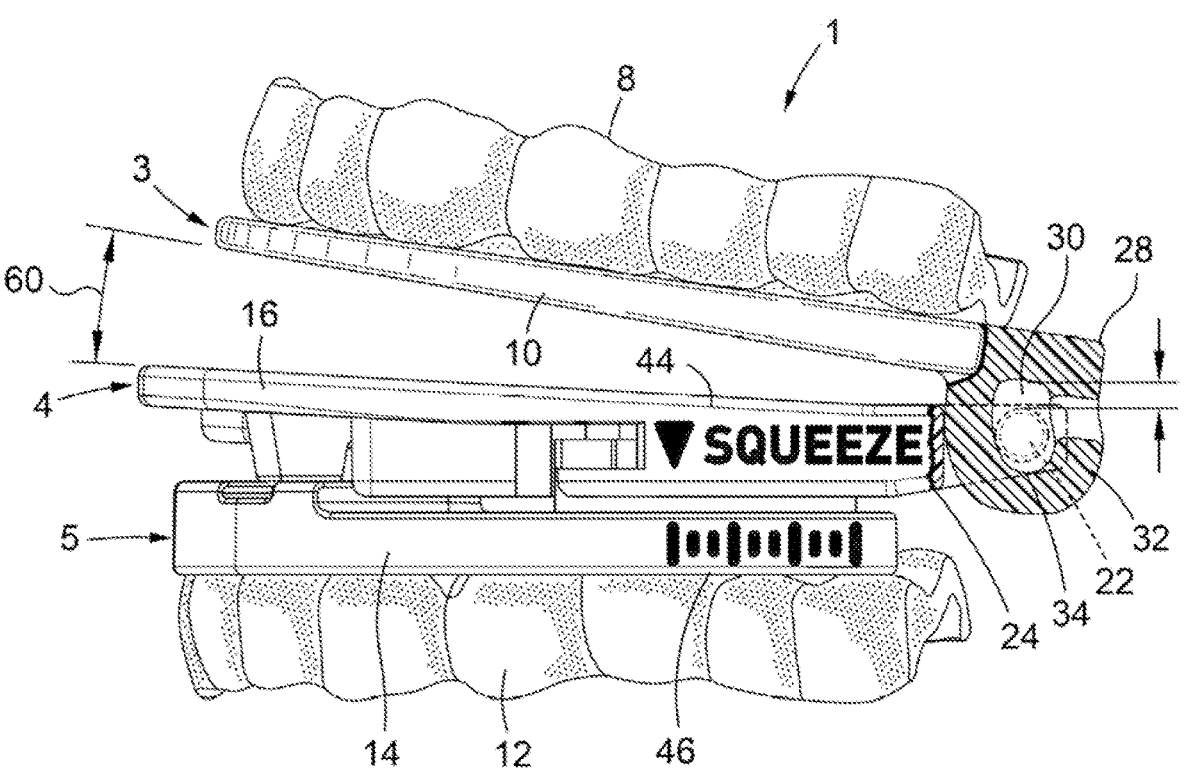

FIG. 10 is a front view of the multi-directional jaw displacement oral appliance when the user's mouth is closed and the upper arch tray assembly lies on the intermediate and lower arch tray assemblies;

FIG. 11 is a side view of the multi-directional jaw displacement oral appliance shown in FIG. 10; and FIG. 12 is a side view of the multi-directional jaw displacement oral appliance when the user's mouth is opened during sleep and the upper arch tray assembly rotates at the hinge shown in FIG. 9 in a vertical direction relative to the intermediate and lower arch tray assemblies.

DESCRIPTION OF THE PREFERRED EMBODIMENT

Turning to the drawings, details are provided of a multi-directional jaw displacement oral appliance 1 that is sized to fit within the mouth and over the teeth of a user so that the user's lower jaw can be selectively repositioned (i.e., advanced) by a variable distance in a horizontal direction relative to the user's upper jaw as is necessary to maintain an open airway to the user's throat in order to reduce the effects of snoring and sleep apnea when the user wears the oral appliance over his teeth while sleeping. What is more, the user's upper jaw can also be repositioned in both vertical and angular upward directions relative to the user's lower jaw so as to minimize the likelihood that the user's upper set of teeth will pull out from the oral appliance in the event that the user's mouth is opened wide while asleep wearing the oral appliance over his teeth. It may therefore be appreciated that the oral appliance 1 has application for use by one wishing to have an adjustable device to enable the user to cope with the effects of snoring and/or sleep apnea and minimize the chance that the oral appliance will become separated from the user's upper set of teeth which could negatively impact the efficacy of the appliance should the user's mouth be opened during sleep.

Referring initially to FIGS. 1-6 of the drawings, the multi-directional jaw displacement oral appliance 1 is shown including an upper arch tray assembly 3 and a lower arch tray assembly 5 that are held one above the other to create a continuous air path through the oral appliance to the user's throat. A flexible intermediate arch tray assembly 4 lies between the upper and lower arch tray assemblies 3 and 5. As will be disclosed in greater detail hereinafter, the upper, intermediate and lower arch tray assemblies 3-5 are coupled to one another such that the lower arch tray assembly 5 can be moved by the user in a horizontal direction back and forth relative to the upper and intermediate arch tray assemblies 3 and 4. Moreover, the upper arch tray 3 can be rotated through an angle as well as moved vertically up and down relative to the intermediate and lower arch tray assemblies 4 and 5.

In the case where the lower arch tray assembly 5 is moved by the user in a horizontal direction back and forth, the user's lower jaw is correspondingly displaced relative to the upper jaw to enable the size of an air path (designated 35 in FIG. 10) through the oral appliance 1 to the user's throat to be selectively adjusted. In the case where the upper arch tray assembly 3 rotates or moves upwardly in a vertical direction, such as when the user opens his mouth during sleep, the user's upper set of teeth will also move upwardly with the upper arch tray assembly 3. By virtue of the foregoing, should the user open his mouth wide while asleep, his upper set of teeth are likely to remain in engagement with the upper arch tray assembly 3 so that the horizontal position of the user's lower jaw relative to his upper jaw will be maintained throughout the night.

The upper arch tray assembly 3 of the multi-directional jaw displacement appliance 1 includes an upper tooth impression liner 8 and an upper liner receiving tray 10 that are preferably manufactured as a single piece by means of a 3-D printing process so that the tooth impression liner 8 is affixed to the top of the upper liner receiving tray 10. Each of the upper tooth impression liner 8 and the upper liner receiving tray 10 has a generally arcuate (i.e., curved) configuration to match the bite pattern of the user's set of teeth carried by his upper jaw.

The lower arch tray assembly 5 of the multi-directional jaw displacement appliance 1 includes a lower tooth impression liner 12 and a lower liner receiving tray 14 that are bonded together so that the liner receiving tray 14 is held in place on top of the lower tooth impression liner 12. In the alternative, the lower tooth impression liner 12 and the lower liner receiving tray 14 can also be manufactured as a single piece by means of a 3-D printing process. As in the case of the upper tooth impression liner 8 and the upper liner receiving tray 10, each of the lower tooth impression liner 12 and the lower liner receiving tray 14 has a generally arcuate (i.e., curved) configuration to match the bite pattern of the user's set of teeth carried by his lower jaw.

The intermediate arch tray assembly 4 includes a flexible hinge attachment tray 16 that is attached to the upper liner receiving tray 10 of the upper arch tray assembly 3 in a manner that will soon be described. The hinge attachment tray 16 of the intermediate arch tray assembly 4 also has a generally arcuate (i.e., curved) configuration to match the arcuate configuration of the upper and lower liner receiving trays 10 and 14 of the upper and lower arch tray assemblies 3 and 5.

As is shown in the drawings, each of the arcuate upper, intermediate and lower arch tray assemblies 3-5 of the oral appliance 1 as well as the upper and lower liner receiving trays 10 and 14 and the hinge attachment tray 16 thereof has a curved closed front end and a pair of opposite sides that are spaced from one another at an open rear end. An upper bite channel 18 (best shown in FIG. 3) runs around the top of the upper tooth impression liner 8 of the arcuate upper arch tray assembly 3. The upper bite channel 18 is sized to receive therewithin the upper set of teeth of the user carried by the user's upper jaw. A lower bite channel 20 (best shown in FIG. 4) runs around the bottom of the lower tooth impression liner 12 of the arcuate lower arch tray assembly 5. The lower bite channel 20 is sized to receive therewithin the lower set of teeth of the user carried by the user's lower jaw.

As an important feature of the multi-directional jaw displacement oral appliance 1, a pair of flexible coupling pins 22 are located within a pin pocket 24 that is formed at each of the opposite sides and at the open rear end of the arcuate hinge attachment tray 16 of the intermediate arch tray assembly 4. Each pair of coupling pins 22, which are separated from one another by a gap 26, extends in axial alignment towards one another across the respective pin pockets 24. A cylindrical coupling catch 28 depends from each of the opposite sides and at the open rear end of the arcuate upper liner receiving tray 10 of the upper arch tray assembly 3. A catch hole 30 runs laterally through each coupling catch 28.

Referring now to FIGS. 5-9 of the drawings, details are provided by which the pairs of flexible coupling pins 22 within the pin pockets 24 of the intermediate and tray assembly 4 are pivotally connected to the cylindrical coupling catches 28 of the upper arch tray assembly 3 so as to create hinges 34 around which the upper arch tray assembly 3 can rotate upwardly through an angle and move up and down in a vertical direction. More particularly, the upper and intermediate arch tray assemblies 3 and 4 are initially held back-to-back one another (i.e., open end to open end). During assembly of the oral appliance 1, the upper and intermediate arch tray assemblies 3 and 4 are then pushed towards one another until the pairs of coupling pins 22 within the pin pockets 24 of the intermediate arch tray assembly 4 are received by and snapped into interlocking engagement with the coupling catches 28 of the upper arch tray assembly 3 at the catch holes 30 thereof (best shown in FIGS. 8 and 9).

The outermost end 32 of each coupling catch 28 is thinned to facilitate the movement of the coupling pins 28 into the coupling catches 28 and past the thinned ends 32, whereby pins 22 are captured by and rotatable within the catch holes 30. The pairs of flexible coupling pins 22 are capable of bending away from one another in order to accommodate the receipt of the thinned outermost ends 32 of the coupling catches 28 through the gaps 26 between each pair of pins 22. With the coupling pins 22 snapped into interlocking engagement with the coupling catches 28, the upper arch tray assembly 3 cannot be inadvertently separated from the intermediate arch tray assembly 4.

FIG. 12 of the drawings shows one hinge 34 that is created when one of the pairs of coupling pins 22 of the intermediate arch tray assembly 4 is moved (i.e., snapped) into receipt by the catch hole 30 of a corresponding one of the cylindrical coupling catches 28 of the upper arch tray assembly 3. As just explained, by virtue of the pair of hinges 34, the pairs of coupling pins 22 are rotatable within the catch holes 30 of respective ones of the coupling catches 30. Accordingly, the upper arch tray assembly 3 and the intermediate arch tray assembly 4 are pivotally coupled to one another such that the upper arch tray assembly 3 is rotatable relative to the intermediate and lower arch tray assemblies 4 and 5.

Continuing to refer to FIG. 12, the multi-directional jaw displacement oral appliance 1 is shown with the upper arch tray assembly 3 rotating at hinges 34 (only one of which being shown) in a generally vertically direction relative to the intermediate and lower arch tray assemblies 4 and 5 in the event that a user opens his mouth while asleep during the night. That is, the cylindrical coupling catches 28 are adapted to rotate around the coupling pins 22 so that the closed front end of the upper arch tray assembly 3 which is engaged by the user's upper set of teeth will pivot through an angle in one of the directions indicated by the reference arrows 60 depending upon whether the user opens or closes his mouth. By virtue of the foregoing, the user's upper set of teeth are less likely to become separated from and "step out" of the oral appliance 1 should the user's mouth be continuously opened and closed throughout the night.

As just explained, the upper arch tray assembly 3 is pivotally and hingedly connected to the intermediate arch tray assembly 4 when the flexible coupling pins 22 are snapped into their interlocking engagement at the catch holes 30 of the coupling catches 28. In this regard, the coupling pins 22 are held in place within the catch holes 30 to prevent an inadvertent removal of the pins 22 from the coupling catches 28 and a separation of the upper arch tray assembly 3 from the intermediate arch tray assembly 4. This connection advantageously avoids the potential of the upper arch tray assembly floating free in the user's mouth during the night.

Still referring to FIG. 10, it should be appreciated that each catch hole 30 of each coupling catch 28 of the upper arch tray assembly 3 within which a pair of locking pins 22 of the intermediate arch tray 4 is pivotally received is higher than the cross section of the catch hole. This elongated dimension creates a space at the top of the catch hole 30 that lies above the locking pins 22. Accordingly, the pair of locking pins 22 can move vertically upward (and downward) through the catch holes 30 to compensate for the locking catches 28 at the rear end of the upper arch tray assembly 3 being pulled upwardly and away from the locking pins 22 at the rear end of the intermediate arch tray assembly 4.

FIGS. 10 and 11 show the multi-directional jaw displacement oral appliance 1 at rest as it would appear while being worn by a user who is asleep with his upper set of teeth located in the upper tooth impression liner 8 of the upper arch tray assembly 3 and his lower set of teeth located in the lower tooth impression liner 12 of the lower arch tray assembly 5. In this case, the user's mouth is closed, such that the upper arch tray assembly 3 lays on top of and is separated from the intermediate arch tray assembly 4 by a short distance.

FIG. 12 shows the multi-directional jaw displacement oral appliance 1 as it is worn when the user's mouth is opened while asleep. Because the open rear end of the arcuate upper arch tray assembly 3 is pivotally connected to the open rear end of the intermediate arch tray assembly 4 by means of the hinges 34, and depending upon how wide the user's mouth is opened, the closed front end of the upper arch tray assembly 3 rotates at the hinges 34 upwardly with the user's upper set of teeth through an angle of about 30-45 degrees as represented by the directional arrows 60. Accordingly, the upper arch tray assembly 3 now pivots away from the intermediate arch tray assembly 4 to increase the separation therebetween by a longer distance with respect to the initial separation shown in FIGS. 10 and 11. By virtue of the foregoing, and as was explained above, the user's upper set of teeth are less likely to step out from the upper upper tooth impression liner 8 of the upper arch tray assembly 3. Otherwise, the oral appliance 1 could separate from the user's upper set of teeth and adversely affect the positioning of the user's lower jaw relative to the upper jaw as well as the user's breathing if the user's mouth is repeatedly opened and closed throughout the night.

Figures 1, 2:
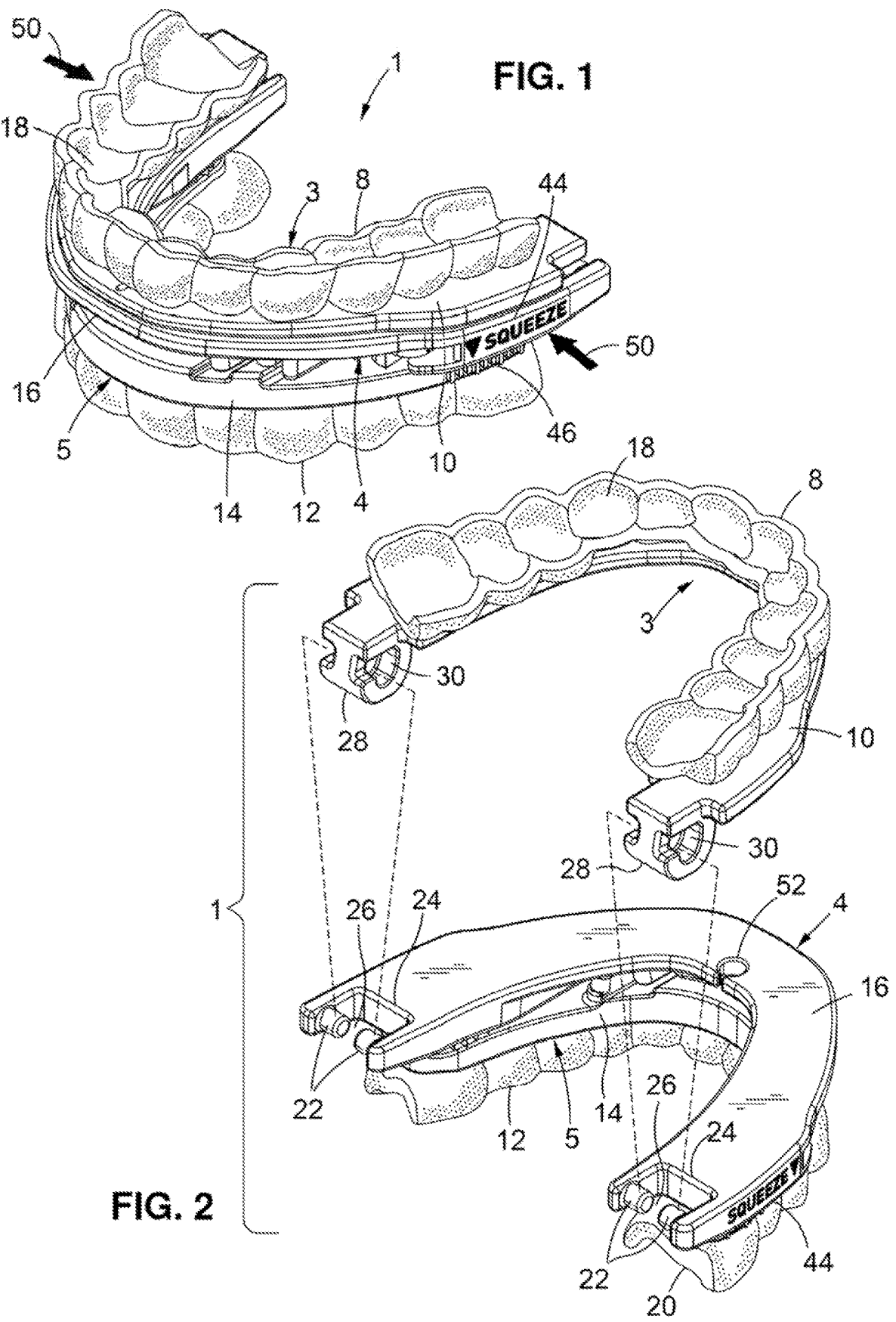
FIG. 1 is a front perspective view of a multi-directional jaw displacement oral appliance according to a preferred embodiment of this invention.
FIG. 2 is an exploded view of the multi-directional jaw displacement oral appliance of FIG. 1.
Figure 3:
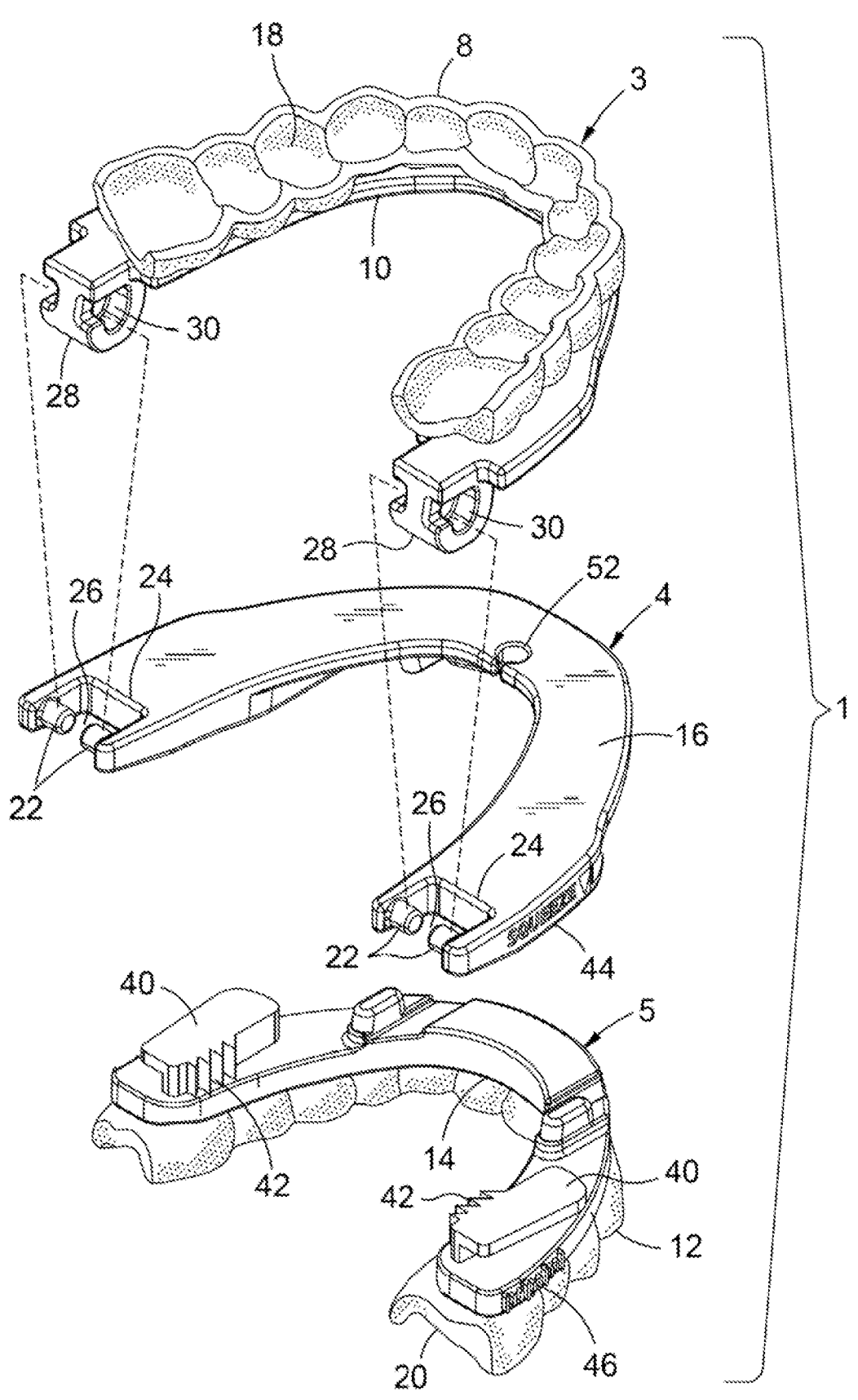
FIG. 3 is an exploded top view showing upper, lower and intermediate arch tray assemblies of the multi-directional jaw displacement oral appliance of FIG. 1.
Figure 4:
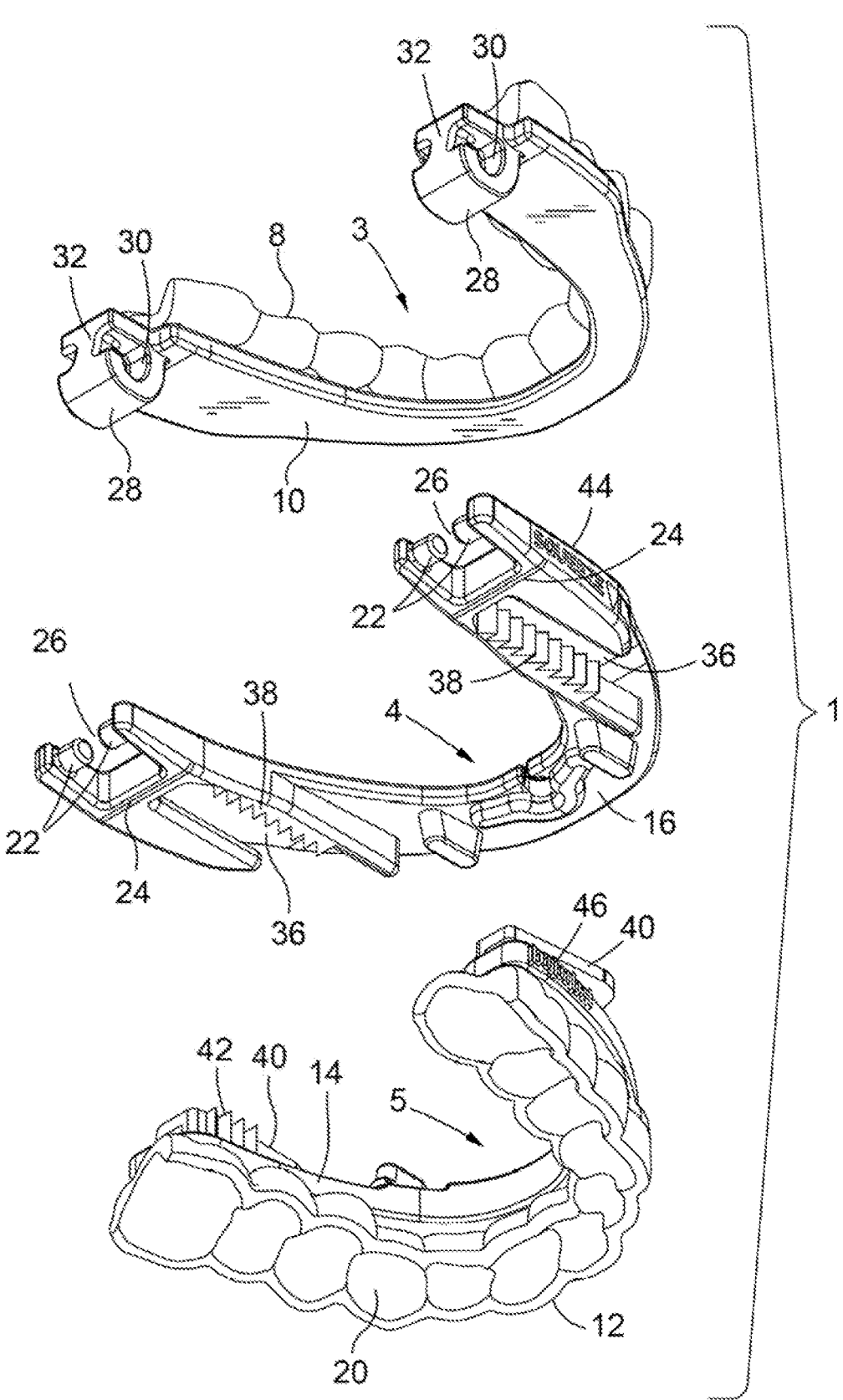
FIG. 4 is an exploded bottom view showing the upper, lower and intermediate arch tray assemblies of the multi-directional jaw displacement oral appliance of FIG. 1.
Figures 5, 6:
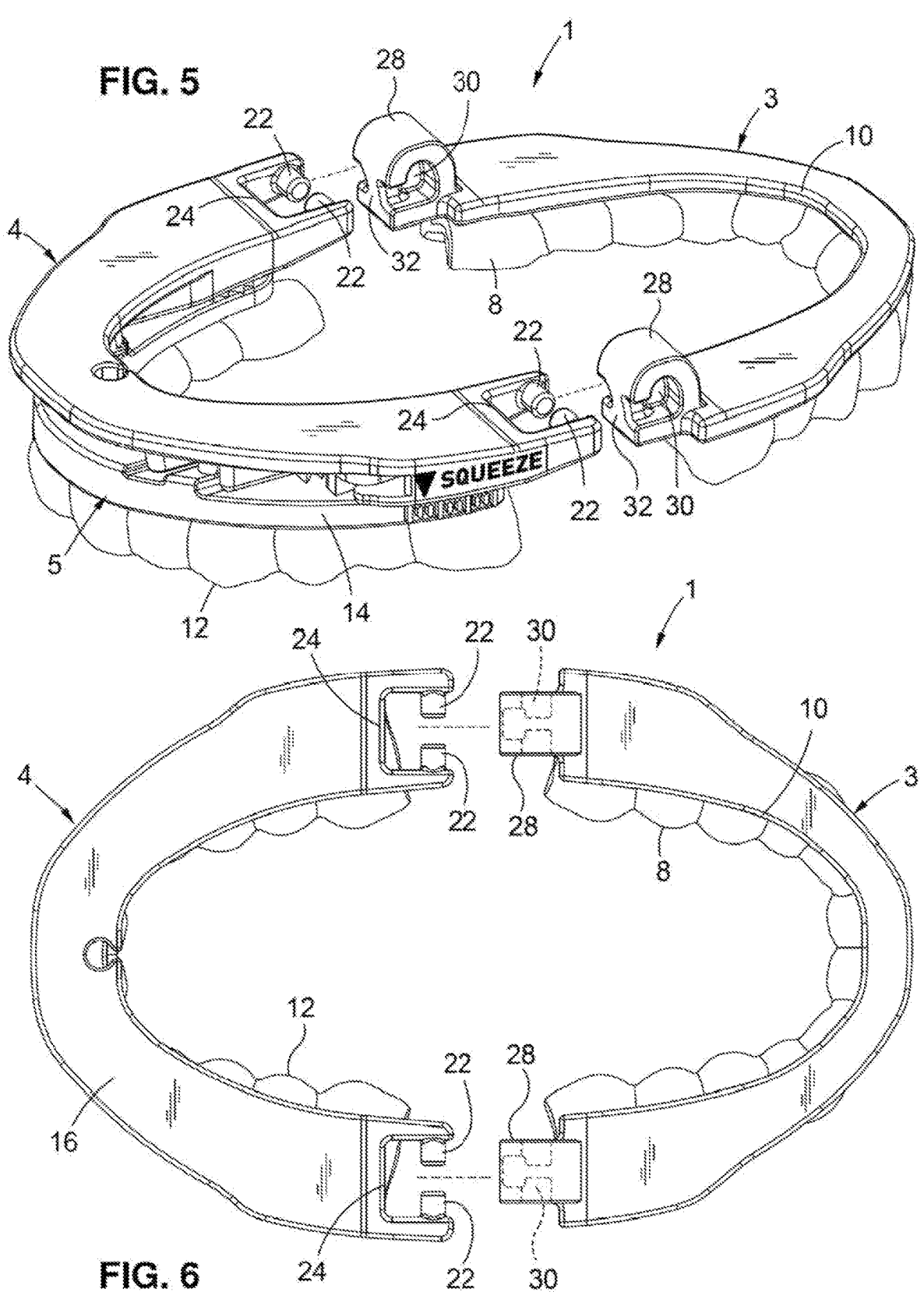
FIG. 5 shows a bottom perspective view of the multi-directional jaw displacement oral appliance during assembly with the intermediate arch tray assembly moving towards the upper arch tray assembly.
FIG. 6 is a bottom view of the multi-directional jaw displacement oral appliance shown in FIG. 5.
Figure 7:
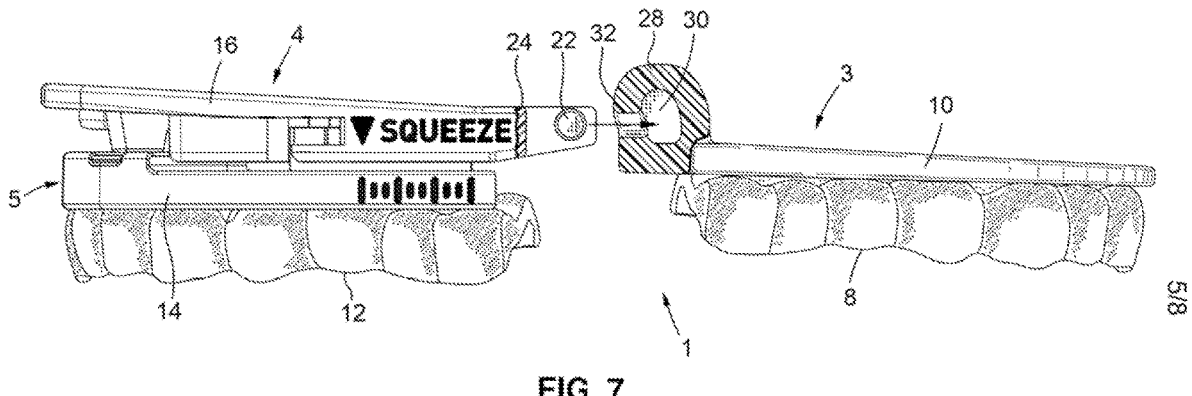
FIG. 7 shows one of a pair of coupling pins of the intermediate arch tray assembly being pivotally connected to a corresponding one of a pair of coupling catches of the upper arch tray assembly.
Figure 8:
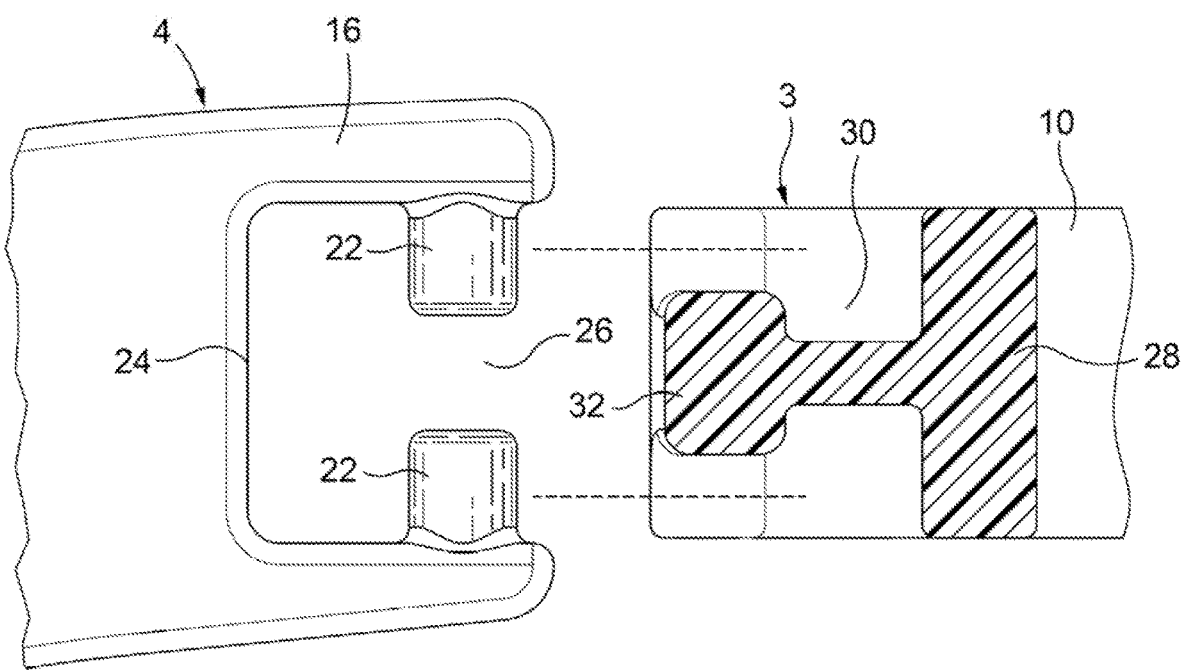
FIG. 8 is an enlarged detail showing one pair of coupling pins of the intermediate arch tray assembly being pivotally connected to one coupling catch of the upper arch tray assembly.

Referring now to FIGS. 3 and 4 of the drawings, details are provided of the means by which the intermediate arch tray assembly 4 of the multi-directional jaw displacement oral appliance 1 is coupled to the lower arch tray assembly 5 such that the lower arch tray assembly 5 as well as the user's lower jaw and the user's lower set of teeth that are located in the lower bite channel 20 of the lower tooth impression liner 12 can be moved back and forth relative to the intermediate arch tray assembly 4 and the upper arch tray assembly 3 as well as the user's upper jaw and the user's upper set of teeth that are located in the upper bite channel of the upper tooth impression liner 8. By virtue of the foregoing, the position of the user's lower jaw can be selectively adjusted along a horizontal direction relative to the position of the user's upper jaw to correspondingly adjust the horizontal advancement of the lower jaw and the size of the air path (designated 35 in FIG. 5) that runs to the user's throat.

As is best shown in FIG. 4, a recessed locking channel 36 is formed (e.g., molded) into the bottom and at each side of the arcuate hinge attachment tray 16 of the intermediate arch tray assembly 4. The locking channels 36 run parallel to one another. A row of teeth 38 is formed (e.g., molded) along one side of each locking channel 36. Located at opposite sides of and standing upwardly from the top of the arcuate lower liner receiving tray 14 of the lower arch tray assembly 5 are a pair of position adjustment blocks 40. A row of teeth 42 (best shown in FIG. 3) is formed (e.g., molded) along one side of each position control block 40.

During the assembly of the multi-directional jaw displacement oral appliance 1, the lower liner receiving tray 14 of the lower arch tray assembly 3 is mounted against the bottom of the hinge attachment tray 16 of the intermediate arch tray assembly 4. To accomplish the foregoing, the pair of position adjustment blocks 40 which stand upwardly from the lower liner receiving tray 14 are pushing into slidable receipt by respective ones of the pair of locking channels 36 that are formed in the bottom of the coupler attachment tray 16, whereby the opposing trays 16 and 14 of the intermediate and lower arch tray assemblies 4 and 5 are coupled together and held in place one over the other. In this same regard, the rows of teeth 42 which run along one side of the pair of upstanding position adjustment blocks 40 are moved into releasable locking engagement with and mesh against the rows of teeth 38 of FIG. 4 which run along one side of the pair of recessed locking channels 36. However, it may be appreciated that any suitable interlocking ratchet means may be substituted for the opposing rows of teeth 38 and 42.

By virtue of the foregoing, the user is provided with the ability to release the locking meshing engagement of the teeth 42 of the position adjustment blocks 40 with the teeth 38 of the locking channels 36. That is, the position of the lower arch tray assembly 5 that engages the user's lower jaw can be selectively changed along a horizontal direction relative to the upper and the intermediate arch tray assemblies 3 and 4 that are coupled to one another by the cylindrical coupling catches 28 and the pairs of coupling pins 22.

A pair of position control pads 44 are located at and molded into opposite sides of the coupler attachment tray 16 of the intermediate arch tray assembly 4. As is best shown in FIGS. 3, 4 and 11, a position indication scale 46 is molded into or printed on each side of the lower liner receiving tray 14 of the lower arch tray assembly 5 so as to lie below a position control pad 44. The hinge attachment tray 16 of the flexible intermediate arch tray assembly 4 is responsive to momentary compressive squeezing forces represented by the directional arrows 50 in FIG. 1 that are simultaneously applied towards one another at the position control pads 44 to temporarily compress and change the shape of the hinge attachment tray 16, whereby the opposite sides of the tray 16 are squeezed together. At the same time, the teeth 38 of the locking channels 36 at the bottom of the flexible hinge attachment tray 16 are temporarily moved out of their former locking engagement with the teeth 42 formed on the position adjustment blocks 40 at the top of the lower liner receiving tray 14. A keyhole notch (designated 52 in FIG. 3) is formed in the hinge attachment tray 16 of the intermediate arch tray assembly 4 midway around the curved front end thereof to facilitate an even compression of the opposite sides of tray 16 towards one another in response to the squeezing forces applied thereto.

The user can now apply a pushing (or pulling) force to change the position of the lower arch tray assembly 5 and thereby advance the user's lower jaw in the horizontal direction as represented by the directional arrows 52 shown in FIG. 11. In this case, the lower arch tray assembly 5 is displaced relative to both the upper and intermediate arch tray assemblies 3 and 4. By selectively changing the position of the lower arch tray assembly 5 in a horizontal direction relative to the upper arch tray assembly 3, the position of the user's lower jaw is correspondingly moved forwards or backwards relative to the upper jaw to vary the size of the air path 35 (of FIG. 10) to the user's throat as may be necessary over time.

After the position of the lower arch tray assembly 5 has been adjusted relative to the position of the upper liner receiving tray 10 of the upper arch tray assembly 3, the momentary compressive squeezing forces 50 are terminated. Accordingly, the formerly compressed hinge attachment tray 16 of the intermediate arch tray assembly 4 will automatically expand back to its initial arcuate shape. At the same time, the teeth 38 of the locking channels 36 will move back into their mating interlocking engagement with the opposing teeth 42 of the position adjustment blocks 40 so that the intermediate and lower arch tray assemblies 4 and 5 will once again be held in place connected one above the other. The location of the position control pads 44 above the position indication scale 46 provides the user with a visual indication of the position of the lower arch tray assembly 5 with respect to the upper and the intermediate arch tray assemblies 3 and 4 so that the user can make regular controllable and precise horizontal position adjustments of the lower arch tray assembly 5 to correspondingly change the position of his or her lower jaw relative to the upper jaw.

It has just been described herein that the lower arch tray assembly 5 is moved in a horizontal direction relative to the upper arch tray assembly 3 once compressive squeezing forces have been applied to the position control pads 44 at opposite sides of the hinge attachment tray 16 of the intermediate arch tray assembly 4. However, it is to be expressly understood that the upper arch tray assembly 3 can be grasped and moved in the same horizontal direction relative to the lower arch tray assembly 5 after the coupler attachment tray 16 is first compressed. In this case, the user's upper jaw will be positioned forwards and backwards relative to the user's lower jaw.

The invention claimed is:

1. A jaw displacement oral appliance configured to be inserted in a month of a user to adjust the position of the user's lower jaw relative to the user's upper jaw so as to maintain an open airway to the user's throat through which the user can breathe while sleeping, said jaw displacement oral appliance comprising:

an upper arch tray assembly having an upper tooth impression liner configured to receive an upper set of teeth of the user's upper jaw during sleep;

a lower arch tray assembly having a lower tooth impression liner configured to receive a lower set of teeth of the user's lower jaw during sleep;

an intermediate arch tray assembly lying between said upper and said lower arch tray assemblies and being attached to said lower arch tray assembly, and each of said upper, said intermediate and said lower arch tray assemblies having a pair of sides that are spaced from and lie opposite one another; and a first coupler including a catch located at each of the pair of sides of said upper arch tray assembly and a second coupler located at each of the pair of sides of said intermediate arch tray assembly and including at least one pin, the pins of said second couplers being snapped into interlocking engagement with respective ones of the catches of said first couplers, whereby said upper and said intermediate arch tray assemblies are pivotally connected together to establish a hinge at which the catches of said first couplers rotate around the pins of said second couplers and said upper arch tray assembly rotates with the user's upper set of teeth through an angle relative to said intermediate and lower arch tray assemblies such that said upper arch tray assembly pivots upwardly at said hinge and away from each of said intermediate and lower arch tray assemblies and the user's lower set of teeth when the user's mouth is opened during sleep, said intermediate arch tray assembly being attached to said lower arch tray assembly so that said lower arch tray assembly moves with the user's lower set of teeth in a horizontal direction relative to each of said intermediate arch tray assembly and said upper arch trat assembly that is connected to said intermediate arch tray assembly, whereby to correspondingly adjust the position of the user's lower jaw relative to the position of the user's upper jaw.

2. The jaw displacement oral appliance recited in claim 1, wherein the second coupler at each of the pair of sides of said intermediate arch tray assembly includes a pair of pins that are axially aligned with one another to be received by and snapped into said interlocking engagement with the each of each of said first couplers.

3. The jaw displacement oral appliance recited in claim 2, wherein the catch of each first coupler has a laterally extending catch hole and the pair of axially aligned pins of each second coupler is received within said catch hole at which to be snapped into said interlocking engagement with said catch so as to prevent a separation of said upper arch tray assembly from said intermediate arch tray assembly.

4. The jaw displacement oral appliance recited in claim 3, wherein the pair of axially aligned pins of each second coupler are flexible so as to bend away from one another in order to accommodate the catch of each first coupler moving therebetween by which to enable each pair of pins to be received by said catch within the catch hole thereof.

5. The jaw displacement oral appliance recited in claim 3, wherein the catch hole of each first coupler is higher in a vertical direction than a cross section in the vertical direction of each of the pair of axially aligned pins of each second coupler received within said catch hole, such that said pair of pins are slidable vertically upward through said catch holes.

6. The jaw displacement oral appliance recited in claim 2, wherein each pair of axially aligned pins of said second couplers are separated from one another by a gap, and respective ones of the catches of said first couplers are configured to move through said gaps so that said pairs of axially aligned pin are snapped into said interlocking engagement with said catches.

7. The jaw displacement oral appliance recited in claim 1, wherein said lower arch tray assembly has a position adjustment block located at each of the pair of sides thereof and said intermediate arch tray assembly has a locking channel located at each of the pair of sides thereof, said position adjustment blocks being received within and slidable through respective ones of said locking channels when said lower arch tray assembly moves in said horizontal direction relative to each of said intermediate arch tray assembly and said upper arch tray assembly that is connected to said intermediate arch tray assembly.

8. The jaw displacement oral appliance recited in claim 7, wherein each position adjustment block and each locking channel located at each pair of sides of the lower and the intermediate arch tray assemblies has a set of teeth, the sets of teeth of said position adjustment blocks and said locking channels lying in meshing engagement with one another, whereby said lower arch tray assembly and said intermediate arch tray assembly are mated in releasable locking engagement with one another.

9. The jaw displacement oral appliance recited in claim 8, wherein said intermediate arch tray assembly is responsive to compressive squeezing forces being simultaneously applied to the pair of sides thereof to compress said intermediate arch tray assembly and thereby move the sets of teeth of said rocking channels out of their meshing engagement with the sets of teeth of the position adjustment blocks to enable said position adjustment blocks to slide through said locking channels and said lower arch tray assembly to move in said horizontal direction relative to each of said intermediate arch tray assembly and said upper arch tray assembly that is connected to said intermediate arch tray assembly.

10. The jaw displacement oral appliance recited in claim 1, wherein each of said upper, said intermediate and said lower arch tray assemblies has an arcuate configuration with a curved front that matches a bite pattern of the user's upper and lower sets of teeth.

11. The jaw displacement oral appliance recited in claim 1, wherein the pins of said second couplers located at each of the pair of sides of said intermediate arch tray assembly are snapped into said interlocking engagement with respective ones of the catches of said first couplers located at each of the pair of sides of said upper arch tray assembly to establish the hinges at which said upper arch tray assembly is rotated relative to said intermediate and said lower arch tray assemblies.

12. The jaw displacement oral appliance recited in claim 1, wherein said upper arch tray assembly that is pivotally connected to said intermediate arch tray assembly is unable to become separated and float free from said intermediate arch tray assembly when the user's mouth is opened during sleep.

13. A jaw displacement oral appliance configured to be inserted in a mouth of a user to adjust the position of the user's lower jaw relative to the user's upper jaw so as to maintain an open airway to the user's throat through which the user can breathe while sleeping, said jaw displacement oral appliance comprising:

an upper arch tray assembly including an upper tooth impression liner configured to receive an upper set of teeth of the user's upper jaw during sleep, said upper arch tray assembly having an accurate configuration with a curved front and a pair of sides that are spaced from and lie opposite one another;

a lower arch tray assembly including a lower tooth impression liner configured to receive a lower set of teeth of the user's lower jaw during sleep, said lower arch tray assembly having an arcuate configuration with a curved font and a pair of sides that are spaced from and lie opposite one another; and an intermediate arch tray assembly lying between said upper and said lower arch tray assemblies and having an arcuate configuration with a curved front and a pair of sides that are spaced from and lie opposite one another, said upper, said intermediate and said lower arch tray assemblies lying one above the other, and said upper arch tray assembly having a first coupler located at each of the pair of sides thereof and said intermediate arch tray assembly having a second coupler located at each of said pair of sides thereof and being pivotally connected in interlocking engagement to respective ones of said first couplers to prevent said upper arch tray assembly from being sated from said intermediate arch tray assembly and to establish a hinge at which said upper arch tray assembly is rotated with the user's upper set of teeth through an angle relative to said intermediate and said lower arch tray assemblies such that said upper arch tray assembly pivots upwardly and away from said intermediate and said lower arch tray assemblies and the user's lower set of teeth when the user's month is opened during sleep, wherein the first coupler that is located at each of the sides of said upper arch tray assembly is a catch having a catch hole formed therein and the second coupler that is located at each of the sides of said intermediate arch tray assembly includes a pair of pins that are axially aligned with one another and snapped into receipt by and into said interlocking engagement with said catch at the catch hole thereof so as to establish said hinge at which said upper arch tray assembly is rotated, said catch hole having a size that is higher in a vertical direction than a cross section in the vertical direction of said pair of pins to permit said pair of pins to move vertically through said catch hole and said upper arch tray assembly to correspondingly move up and down relative to said intermediate and lower arch tray assemblies when the user's mouth is opened and closed during sleep.

14. The jaw displacement oral appliance recited in claim 13, wherein each of the pair of pine of the second coupler that is located at each side of said intermediate arch tray assembly is flexible by which to cause said pair of pins to be snapped into said receipt by and said interlocking relationship with the catch at said catch hole thereof to establish said hinge.

* * * * *